United States Patent
Yamauchi et al.

(10) Patent No.: US 7,658,761 B2
(45) Date of Patent: Feb. 9, 2010

(54) BALLOON EXPANDABLE SUPERELASTIC STENT

(75) Inventors: Kiyoshi Yamauchi, Sendai (JP); Kouji Mori, Okayama (JP); Shuzou Yamashita, Okayama (JP)

(73) Assignees: NEC Tokin Corporation, Sendai-shi (JP); Japan Stent Technology Co., Ltd., Okayama-shi (JP)

( * ) Notice: Subject to any disclaimer, the term of this patent is extended or adjusted under 35 U.S.C. 154(b) by 854 days.

(21) Appl. No.: 11/071,516

(22) Filed: Mar. 3, 2005

(65) Prior Publication Data

US 2005/0209683 A1 Sep. 22, 2005

(30) Foreign Application Priority Data

Mar. 5, 2004 (JP) ............... 2004-062664

(51) Int. Cl.
*A61F 2/06* (2006.01)
(52) U.S. Cl. .................................................. 623/1.46
(58) Field of Classification Search ................ 623/1.11, 623/1.15, 1.46; 427/2.24; 424/422–428
See application file for complete search history.

(56) References Cited

U.S. PATENT DOCUMENTS

| | | | |
|---|---|---|---|
| 3,174,851 A | 3/1965 | Buehler et al. | |
| 4,770,725 A | 9/1988 | Simpson et al. | |
| 5,830,179 A | 11/1998 | Mikus et al. | |
| 5,928,217 A | 7/1999 | Mikus et al. | |
| 6,174,305 B1 | 1/2001 | Mikus et al. | |
| 6,312,455 B2 | 11/2001 | Duerig et al. | |
| 7,402,173 B2* | 7/2008 | Scheuermann et al. ..... | 623/1.46 |
| 2002/0082681 A1 | 6/2002 | Boylan et al. | |
| 2004/0172127 A1* | 9/2004 | Kantor ..................... | 623/1.16 |

FOREIGN PATENT DOCUMENTS

| | | |
|---|---|---|
| EP | 0 873 734 A2 | 10/1998 |
| EP | 0 873 734 B1 | 10/2003 |
| JP | 58-161753 | 9/1983 |
| JP | 63-014834 | 1/1988 |
| JP | 63-171844 | 7/1988 |
| JP | 11-042283 | 2/1999 |
| JP | 11-099207 | 4/1999 |
| JP | 2000-508207 A | 7/2000 |
| JP | 2003-062078 A | 3/2003 |
| WO | WO 95/31945 | 11/1995 |
| WO | WO 96 09020 A1 | 3/1996 |

OTHER PUBLICATIONS

Franz Volker, Communication, European Patent Office, Oct. 17, 2006, 4 Pages.

(Continued)

*Primary Examiner*—Kevin T Truong
(74) *Attorney, Agent, or Firm*—Frishauf, Holtz, Goodman & Chick, P.C.

(57) ABSTRACT

A balloon expandable superelastic stent is made of a Ti—Ni—Nb (the content of Nb being at least 3 at %) shape memory alloy. A shape recovery temperature of the stent is lower than a living body temperature in an unloaded state after shape memory treatment. The shape recovery temperature exceeds the living body temperature after the stent is mounted to a catheter and released from the catheter in a living body.

15 Claims, 1 Drawing Sheet

OTHER PUBLICATIONS

EPO Search Report made for EP 05004807.3-2107.

Japanese Office Action dated Feb. 4, 2009 and English translation thereof issued in a counterpart Japanese Application No. 2004-062664.

Australian Office Action dated Oct. 13, 2009 and English translation thereof issued in a counterpart Australian Application No. 2005201000.

* cited by examiner

BALLOON EXPANDABLE SUPERELASTIC STENT

This application claims priority to prior Japanese patent application JP 2004-62664, the disclosure of which is incorporated herein by reference.

BACKGROUND OF THE INVENTION

This invention relates to a stent to be placed in a lumen of a human body or an animal.

As well known, a shape memory alloy, such as a Ti—Ni alloy, exhibits a remarkable shape memory effect in association with martensitic reverse transformation. It is also well known that the shape memory alloy exhibits excellent superelasticity or pseudoelasticity in association with stress-induced martensitic transformation caused by strong deformation in a parent phase, that is, austenite phase after the reverse transformation. The superelasticity is observed in a number of shape memory alloys. Among others, the superelasticity is remarkable in the Ti—Ni alloy and a Ti—Ni—X alloy (X=V, Cr, Co, Nb, or the like) obtained by substituting an element X for a part of the Ti—Ni alloy.

The shape memory effect of the Ti—Ni alloy is described in U.S. Pat. No. 3,174,851 (hereinafter referred to as a patent document 1). The superelasticity of the Ti—Ni alloy is described in Japanese Unexamined Patent Application Publication (JP-A) No. S58-161753 (hereinafter referred to as a patent document 2).

The shape memory effect and the superelasticity of the Ti—Ni—X alloy are described in Japanese Unexamined Patent Application Publications (JP-A) Nos. S63-171844 (hereinafter referred to as a patent document 3) and S63-14834 (hereinafter referred to as a patent document 4) for a Ti—Ni—Nb alloy and in U.S. Pat. No. 4,770,725 (hereinafter referred to as a patent document 5) for a Ti—Ni—Nb alloy. As compared with the Ti—Ni alloy, the Ti—Ni—Nb alloy has a characteristic that transformation temperature hysteresis is increased by imposing a stress. Therefore, the Ti—Ni—Nb alloy is put into practical use as a joint for reactor piping.

Angioplasty using a stent is a technique for treating occlusion or narrowing of a blood vessel or a heart valve. The stent is a mesh-like metal tube or tube to be placed in a living body in order to prevent re-narrowing of a narrow portion, such as a blood vessel, after it is radially expanded. The stent is folded into a small size and mounted to an end portion of a catheter. After introduced into the narrow portion together with the catheter, the stent is released from the catheter and radially expanded to be attached to an inner wall of a lumen such as a blood vessel.

For example, in case of PTCA (percutaneous transluminal coronary angioplasty), the stent is radially expanded following a blood vessel expanding operation by inflation of an internal balloon set on an inner wall of the catheter. The stent is called a balloon expandable stent and formed by the use of a metal such as stainless steel or tantalum.

On the other hand, in order to prevent rupture of an aneurysm which may result in a subarachnoid hemorrhage or the like, blood supply to the aneurysm is stopped. As one of techniques for stopping the blood supply, use is made of embolization in which a metal coil such as a platinum coil is implanted into the aneurysm to form a blood clot (thrombus). However, it is pointed out that a part of the blood clot may possibly be released from the metal coil and carried by a bloodstream to a periphery to block a blood vessel. In order to avoid such undesired phenomenon, consideration is made about a covered stent technique in which the aneurysm is embolized by the use of a graft. In this case, simultaneously when the stent is released from the catheter, the stent is radially expanded by its own spring function to press the graft against a blood vessel wall. Such stent is called a self expandable stent. For the self expandable stent, a material having an excellent spring characteristic is desired.

The superelasticity in the Ti—Ni alloy is a behavior that, at a temperature above a reverse transformation finish temperature (Af point, austenitic transformation finish temperature) thereof, the alloy which has been deformed under an external load is recovered into an original shape simultaneously when the external load is released. A recoverable deformation is as high as about 7% in case of an elongation strain. For use as the stent, the alloy is formed into a hoop shape slightly greater in diameter than the lumen where the stent is to be placed. The stent is radially contracted and mounted to the catheter. Simultaneously when the stent is released from the catheter, the stent is autonomously recovered into the diameter of the original hoop shape to be brought into tight contact with the lumen such as the blood vessel. Thus, the alloy has the Af point lower than a living body temperature (37° C.) and always exhibits the superelasticity at the living body temperature.

As well as the above-mentioned characteristics, the superelastic stent has several problems. For example, its own spring function may damage the blood vessel wall and its autonomous shape recovery may cause a positioning error in the lumen. Therefore, it is difficult to use the superelastic stent in a blood vessel system such as a coronary system.

The stent for use in PTCA is preferably made of a metal material having a low spring function and a high rigidity. However, use of such material is disadvantageous in that a force urging a lumen wall outward is weak to cause a positioning error following blood vessel pulsation.

In view of the above, proposal has been made of a stent using a shape memory alloy.

Japanese Unexamined Patent Application Publication (JP-A) No. H11-42283 (hereinafter referred to as a patent document 6) discloses that a Ti—Ni—Nb alloy is applied to a stent. Specifically, the above-mentioned publication describes that the stent made of a Ti—Ni—Nb alloy and having a low Young's modulus upon shape recovery and a high Young's modulus upon shape deformation under an external load is obtained if the ratio of the stress on loading to the stress on unloading at the respective inflection points on the stress-strain curve is at least about 2.5:1. This stent exhibits superelasticity at the living body temperature after it is released from the catheter but does not sufficiently achieve desired positioning of the stent as required in PTCA.

The present inventors have already proposed a stent obtained by slotting in Japanese Unexamined Patent Application Publication (JP-A) No. H11-99207 (hereinafter referred to as a patent document 7). In detail, the patent document 7 proposes the stent which exhibits no shape memory effect at the living body temperature during insertion into the living body and exhibits superelasticity after shape recovery by inflation of a balloon. In the embodiment in the patent document 7, the stent made of a Ti—Ni alloy or a Ti—Ni—X alloy (X=Cr, V, Cu, Fe, Co, or the like) is subjected to strong deformation to thereby elevate a recovery temperature. However, in case of the stent obtained by slotting as shown in the patent document 7, the strong deformation is performed merely by accommodating the heat-treated stent into the catheter. Therefore, depending upon a slot shape, sufficient deformation is difficult and sufficient effect is not obtained.

SUMMARY OF THE INVENTION

It is therefore an object of this invention to provide a stent which can easily be placed not only in a blood vessel but also in a lumen of a human body or an animal.

It is another object of this invention to provide a method which is applicable to production of a stent having a slotted shape.

According to one aspect of this invention, there is provided a balloon expandable superelastic stent, which comprises a Ti—Ni—Nb shape memory alloy, in which the content of Nb is at least 3 at %. The stent has a shape memory temperature lower than a living body temperature in an unloaded state after shape memory treatment. The shape recovery temperature exceeds the living body temperature when the stent is inserted into a living body.

According to another aspect of this invention, there is also provided a method of producing a balloon expandable superelastic stent which comprises a Ti—Ni—Nb shape memory alloy in which the content of Nb is at least 3 at %. The method comprises the steps of slotting a tubular material of the shape memory alloy, expanding the tubular material in a radial direction, subjecting the tubular material to shape memory treatment, and radially contracting the tubular material.

DESCRIPTION OF THE PREFERRED EMBODIMENTS

Figure 1:
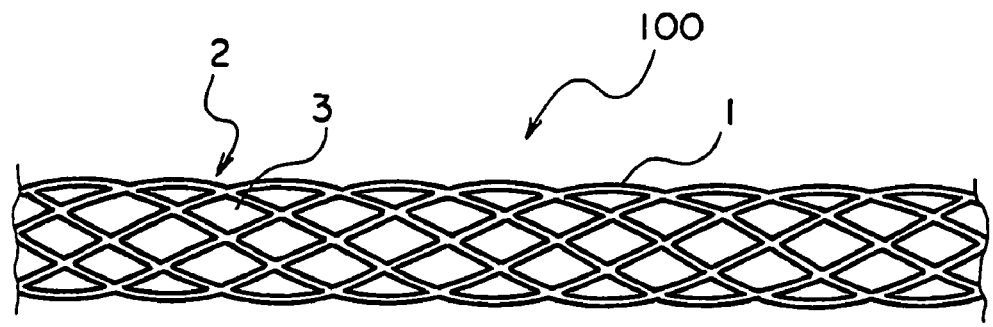
FIG. 1 is a view showing a Ti—Ni—Nb alloy slotted tube according to an embodiment of this invention.

In this invention, a Ti—Ni—Nb alloy is used as a stent material so as to provide a stent which is for use in a blood vessel treatment such as PTCA and which assures a balloon expandable function upon insertion into a living body and a superelastic function while the stent is tightly adhered to a lumen after it is radially expanded.

A balloon expandable superelastic stent of this invention is made of a Ti—Ni—Nb shape memory alloy. In the shape memory alloy, the content of Nb is at least 3 at %. In the stent, a shape recovery temperature in an unloaded state after shape memory treatment is lower than a living body temperature and is higher than the living body temperature when the stent is mounted to a catheter and released from the catheter.

The balloon expandable superelastic stent is radially contracted and mounted to a balloon portion in the catheter and guided to a diseased site. After the stent is released from the catheter, a shape recovery function is exhibited simultaneously with balloon expansion or when the stent is warmed thereafter. After the shape recovery function is exhibited, a shape recovery force is continued at the living body temperature. Herein, warming may be carried out either electrically or thermally. The electrical warming is electric heating, such as resistance heating or induction heating. The thermal warming is, for example, heating using hot water or the like.

The balloon expandable superelastic stent mentioned above is processed into a mesh tube, subjected to shape memory treatment, and mounted to the catheter after a strain of 8% or more is imposed. Herein, the stent as the mesh tube is produced by forming a wire material into a mesh pattern or processing a tube into a mesh pattern by laser machining or etching. In this invention, the strain is imposed by elongation, bending, compression, or shearing.

The balloon expandable superelastic stent may be mounted to the catheter after the strain of at least 8% is imposed by mechanical expansion.

The balloon expandable superelastic stent may be mounted to the catheter after the strain of at least 8% is imposed by mechanical radial contraction.

In this invention, a superelastic stent having a balloon expandable function is obtained by forming a Ti—Ni—Nb alloy material (preferably having a tubular shape) containing 3 at % or more Nb into a predetermined shape and imposing an elongation strain or a bending strain of at least 8%.

Now, description will be made as regards embodiments of this invention with reference to the drawing.

(i) Basic Performance of Alloy

Various kinds of alloys shown in Table 1 were formed into wires having a diameter ($\phi$) of 10 mm. The wires were subjected to shape memory treatment. Then, the alloys were examined about the change in shape recovery temperature caused by imposing the strain. In detail, at temperatures not higher than the reverse transformation start temperatures (As points, austenitic-transformation start temperatures in reverse transformation from the martensite phase to the austenite phase) of the respective alloys, elongation strains $\epsilon=0$, 8, 10, 15, and 20% were imposed. The alloys were immersed into a hot bath and the shape recovery temperatures were examined. In a No. 1 alloy (Ti—Ni alloy) as a comparative example, elevation of the shape recovery temperature caused by imposing the strain is small as compared with Nos. 2-5 alloys (Ti—Ni—Nb alloys) in this invention. If the strain $\epsilon=15\%$ or more is imposed to the No. 1 alloy, the recovery temperature falls within an applicable range of this invention. In this event, however, a permanent strain is introduced and the shape recovery amount after heating is extremely reduced. On the other hand, in the Ti—Ni—Nb alloy, the elevating effect of the recovery temperature by imposing the strain is more remarkable as the content of Nb is increased. However, if the content of Nb is excessively large, plastic workability is deteriorated. Further, imposing a high strain results in a decrease in shape recovery amount, like in the Ti—Ni alloy. In the case of the Ti—Ni—Nb alloy, the shape recovery amount was 80% or more and 60% or more for the strain of up to 8% and 15%, respectively. However, for the strain of 20%, the shape recovery amount was less than 50%. Thus, in this invention, the content of Nb is 3 at % or more, preferably 6-9 at %, and the strain to be imposed is 8% or more, preferably 10-15%.

It has been confirmed that the shape recovery temperature of each sample after shape recovery by heating returns to the shape recovery temperature when no strain is imposed.

TABLE 1

|  | composition (%) | | | shape recovery temperature (° C.) | | | | |
| --- | --- | --- | --- | --- | --- | --- | --- | --- |
|  |  |  |  | $\epsilon =$ | $\epsilon =$ | $\epsilon =$ | $\epsilon =$ | $\epsilon =$ |
| No. | Ni | Ti | Nb | 0% | 8% | 10% | 15% | 20% |
| 1 | 50.7 | 49.3 | 0 | 15 | 15 | 20 | 30 | 40 |
| 2 | 49 | 48 | 3 | 10 | 15 | 30 | 43 | 60 |
| 3 | 49 | 45 | 6 | 10 | 18 | 37 | 55 | 80 |
| 4 | 46 | 42 | 9 | 0 | 25 | 40 | 60 | 90 |
| 5 | 46 | 42 | 15 | −5 | 20 | 45 | 70 | 100 |

(ii) Performance of Slotted Tube

Figure 2:
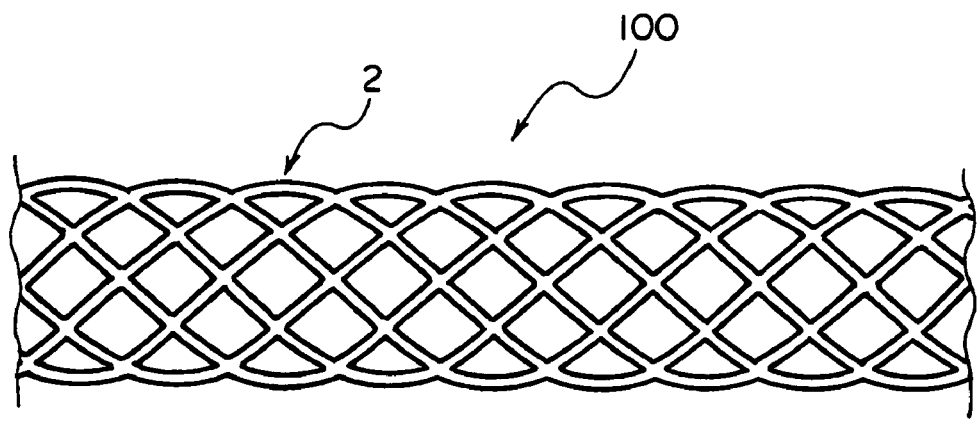
FIG. 2 is a view of the slotted tube in FIG. 1 after mechanically expanded.

Each of tubes of $\phi$5.0 mm of the Nos. 3 and 4 alloys was processed into a slotted shape illustrated in FIG. 1 by laser machining to obtain a stent 100 of a first embodiment. The stent 100 has a shape as a mesh tube 2 formed by a mesh wire 1 having slots 3. The stent 100 was subjected to shape memory treatment. The stent 100 having the shape as the mesh tube 2 was mechanically expanded radially in a dry-ice/alcohol bath at −50° C. into φ5.5 mm (ε=10%) and φ5.75 mm (ε=15%) as illustrated in FIG. 2. Then, the recovery temperature was examined. The result is shown in Table 2. Each tube thus expanded exhibited a temperature characteristic substantially similar to the test result of the above-mentioned wire material. It is therefore understood that, also in the shape of the stent, elevation of the shape recovery temperature by imposing the strain is achieved in the manner similar to the wire material.

Figure 3:
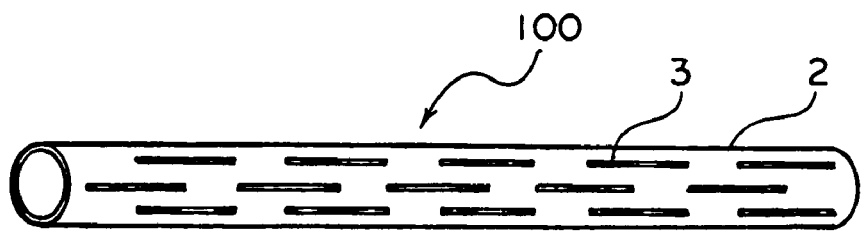
FIG. 3 is a view showing a Ti—Ni—Nb alloy slotted tube according to another embodiment of this invention.

Next, as the stent 100 of a second embodiment, the tube 2 of φ1.2 mm of the No. 4 alloy was provided with the slots 3 in a staggered fashion in a longitudinal direction and in a circumferential direction, as illustrated in FIG. 3. Thereafter, the tube 2 was radially expanded into φ5.0 mm to obtain a mesh tube and subjected to shape memory treatment at 600° C. Then, the tube 2 was radially contracted into φ1.2 mm and subjected to swaging into φ1.05 mm (the strain of about 13%). This tube had a shape recovery temperature of 55° C. Thus, an appropriateness of such strain imposing technique was confirmed.

Further, the slotted tube of φ1.2 mm of the No. 4 alloy in FIG. 3 was radially expanded into φ5.5 mm and subjected to heat treatment. Thereafter, the tube was radially contracted into φ1.2 mm again (the maximum strain of a slot angle was about 10%). The shape recovery temperature was examined and was about 40° C.

TABLE 2

| alloy | expanded diameter (mm) | shape recovery behavior 37° C. | shape recovery temperature |
|---|---|---|---|
| No. 3 | φ5.5 | shape recovered completely | |
| | φ5.75 | no shape change observed | shape recovered at 55° C. |
| No. 4 | φ5.5 | shape recovered slightly, but not completely | shape recovered at 40° C. |
| | φ5.75 | no shape change observed | shape recovered at 60° C. |

(iii) Stent Delivery Test

A catheter equipped with the φ5.5 mm expanded stent of the No. 4 alloy was guided into a blood vessel having a diameter of about 4 mm. The stent was released at the living body temperature (37° C.). As shown in Table 2, the stent was slowly expanded simultaneously when it was released, but was not completely recovered. The stent was expanded by a balloon and fixed to an inner wall of the blood vessel. Thereafter, saline solution at about 45° C. was supplied into the balloon to warm the stent to a temperature of 40° C. or higher.

Next, the φ5.75 mm expanded stent of the No. 4 alloy was tested in the similar manner. At 37° C., no change in shape of the stent was observed. For the purpose of shape recovery, warming was carried out by means of induction heating. Specifically, hot water of 37° C. was circulated through the blood vessel and warming was carried out by the induction heating. The temperature was measured by a thermocouple attached to the stent.

After the experiment, the stent was taken out from the blood vessel to examine any damage of the blood vessel wall caused by heating and the shape recovery temperature of the stent. In either case, no remarkable deterioration of the blood vessel wall was observed and the superelasticity was exhibited at 37° C.

Not being limited to the embodiments, the stent may be restrained by a restraining component such as tungsten, tantalum, or a gold alloy in order to suppress slight shape recovery at the living body temperature. Thus, the functionality and the angiographic effect can be improved. Further, heating for shape recovery of the stent is possible by applying electric current to the above-mentioned restraining component or a conductor wire such as copper and steel.

The optimum shape memory alloy used in this invention is the Ti—Ni—Nb alloy. Alternatively, use may be made of an alloy further containing a fourth element such as Fe, Cr, V, or Co in addition to Ti, Ni, and Nb. As described above, according to this invention, it is possible to provide the stent which can easily be mounted not only to a blood vessel but also to a lumen of a human body or an animal.

The balloon expandable superelastic stent according to this invention is optimum as an apparatus for medical treatment using a stent.

What is claimed is:

1. A balloon expandable superelastic stent comprising a Ti—Ni—Nb shape memory alloy, wherein the content of Nb is at least 3 at %, the stent having been subjected to a shape memory treatment to have a reverse transformation finish temperature (Af point) which is (i) lower than a living body temperature in an unloaded state in which a strain has not been imposed on the shape memory alloy and (ii) higher than the living body temperature after the strain has been imposed on the shape memory alloy.

2. The balloon expandable superelastic stent according to claim 1, wherein the stent is radially contracted and mounted to a balloon portion in a catheter to be guided to a diseased site, wherein the stent recovers its shape by being warmed one of (i) simultaneously with balloon expansion and (ii) after the balloon expansion, and wherein after recovering its shape the stent keeps shape recovery force even at the living body temperature.

3. The balloon expandable superelastic stent according to claim 2, wherein the stent is obtained by one of: (i) forming a wire into a mesh pattern, and (ii) by processing a tube into a mesh pattern by laser machining of etching, and wherein the stent having the mesh pattern is subjected to the shape memory treatment, then subjected to the strain, which is a strain of at least 8%, and then mounted to the catheter.

4. The balloon expandable superelastic stent according to claim 3, wherein the strain is 10-15%.

5. The balloon expandable superelastic stent according to claim 2, wherein the strain is a strain of at least 8% that is imposed by mechanical expansion of the stent, and the stent is mounted to the catheter after the strain is imposed.

6. The balloon expandable superelastic stent according to claim 2, wherein the strain is a strain of at least 8% that is imposed by mechanical radial contraction of the stent, and the stent is mounted to the catheter after the strain is imposed.

7. The balloon expandable superelastic stent according to claim 1, wherein the stent is obtained one of:

(i) by forming a wire into a mesh pattern, and (ii) by processing a tube into a mesh pattern by laser machining or etching, and wherein the stent having the mesh pattern is subjected to the shape memory treatment and then subjected to the strain, which is a strain of at least 8%.

8. The balloon expandable superelastic stent according to claim 7, wherein the strain is 10-15%.

9. The balloon expandable superelastic stent according to claim 1, wherein the strain is a strain of at least 8% that is imposed by mechanical expansion of the stent.

10. The balloon expandable superelastic stent according to claim 1, wherein the strain is a strain of at least 8% that is imposed by mechanical radial contraction of the stent.

11. The balloon expandable superelastic stent according to claim 1, wherein the content of Nb is 6-9 at %.

12. A method of producing a balloon expandable superelastic stent, the method comprising:

slotting a tubular material of a Ti—Ni—Nb shape memory alloy in which the content of Nb is at least 3 at %;

expanding the tubular material in a radial direction;

subjecting the tubular material to shape memory treatment;

imposing a strain on the shape memory alloy, at a temperature that is not higher than a reverse transformation start temperature (As point) of the shape memory alloy; and radially contracting the tubular material;

wherein (i) after the shape memory treatment but before the strain is imposed, the shape memory alloy has a reverse transformation finish temperature (Af point) that is lower than a living body temperature, and (ii) after the shape memory treatment and after the strain is imposed, the shape memory alloy has a reverse transformation finish temperature (Af point) that is higher than a living body temperature.

13. The method according to claim 12, wherein the strain is a strain of at least 8%.

14. The method according to claim 13, wherein the strain is 10-15%.

15. The method according to claim 12, wherein the content of Nb is 6-9 at %.

* * * * *